(12) United States Patent
Hayman et al.

(10) Patent No.: US 8,998,798 B2
(45) Date of Patent: Apr. 7, 2015

(54) MULTI-LUMEN TRACHEAL TUBE WITH VISUALIZATION DEVICE

(75) Inventors: Sarah Hayman, Boulder, CO (US); Lockett E. Wood, Lyons, CO (US); Neville DeWitt Pierrat, Golden, CO (US); Steven J. Grate, St. Peters, MO (US); Jonathan Bloom, Boulder, CO (US); Roger Mecca, Corona Del Mar, CA (US); Alissa Wong, Boulder, CO (US); Christina Kornreich, Boulder, CO (US); Susan Roweton, Boulder, CO (US); Shannon E. Campbell, Boulder, CO (US); Mark R. Behlmaier, Erie, CO (US)

(73) Assignee: Covidien LP, Mansfield, MA (US)

(*) Notice: Subject to any disclaimer, the term of this patent is extended or adjusted under 35 U.S.C. 154(b) by 547 days.

(21) Appl. No.: 12/981,296

(22) Filed: Dec. 29, 2010

(65) Prior Publication Data
US 2012/0172664 A1     Jul. 5, 2012

(51) Int. Cl.
| A61B 1/04 | (2006.01) |
| A61M 16/04 | (2006.01) |
| A61B 1/00 | (2006.01) |
| A61B 1/05 | (2006.01) |
| A61B 1/12 | (2006.01) |
| A61B 1/267 | (2006.01) |

(52) U.S. Cl.
CPC ............ *A61M 16/04* (2013.01); *A61B 1/00082* (2013.01); *A61B 1/05* (2013.01); *A61B 1/127* (2013.01); *A61B 1/2676* (2013.01); *A61M 16/0404* (2014.02); *A61M 16/0459* (2014.02); *A61M 16/0486* (2014.02); *A61B 1/00045* (2013.01); *A61M 2205/502* (2013.01); *A61M 2205/3306* (2013.01)

(58) Field of Classification Search
USPC .......................................... 600/170–171, 194
See application file for complete search history.

(56) References Cited

U.S. PATENT DOCUMENTS

| 1,595,050 | A | * | 8/1926 | Wolf ............................. 600/107 |
| 4,233,984 | A | | 11/1980 | Walling |
| 4,453,545 | A | * | 6/1984 | Inoue ....................... 128/207.15 |
| 4,685,457 | A | | 8/1987 | Donenfeld |
| 4,688,568 | A | * | 8/1987 | Frass et al. ............... 128/207.15 |

(Continued)

FOREIGN PATENT DOCUMENTS

| WO | 2008103448 A1 | 8/2008 |
| WO | 2010091440 A2 | 8/2010 |

OTHER PUBLICATIONS

PCT/US2011/063492 International Search Report and Written Opinion mailed Apr. 2, 2012.

(Continued)

*Primary Examiner* — Matthew J Kasztejna
(74) *Attorney, Agent, or Firm* — Fletcher Yoder PC

(57) ABSTRACT

The present disclosure describes systems and methods that utilize a multi-lumen tube with an integral visualization apparatus, such as a camera. The multi-lumen tracheal tube system may include a camera apparatus that is positioned to facilitate left or right bronchial intubation. In addition, the camera apparatus may be a unitary assembly that functions to hold and position the camera relative to the tube and provides an acceptable profile for comfortable intubation. The camera apparatus may include additional components, such as integral light sources and flushing or cleaning devices to remove any buildup from the camera or optical components.

17 Claims, 8 Drawing Sheets

(56) References Cited

U.S. PATENT DOCUMENTS

| | | | |
|---|---|---|---|
| 4,846,153 A | 7/1989 | Berci | |
| 4,949,716 A | 8/1990 | Chenoweth | |
| 4,982,729 A | 1/1991 | Wu | |
| 5,016,614 A | 5/1991 | MacAllister | |
| 5,038,766 A | 8/1991 | Parker | |
| 5,174,283 A | 12/1992 | Parker | |
| 5,203,320 A | 4/1993 | Augustine | |
| 5,259,377 A | 11/1993 | Schroeder | |
| 5,285,778 A | 2/1994 | Mackin | |
| 5,329,940 A | 7/1994 | Adair | |
| 5,339,805 A | 8/1994 | Parker | |
| 5,363,838 A | 11/1994 | George | |
| 5,400,771 A * | 3/1995 | Pirak et al. | 600/109 |
| 5,499,625 A * | 3/1996 | Frass et al. | 128/207.15 |
| 5,607,386 A | 3/1997 | Flam | |
| 5,636,625 A | 6/1997 | Miyagi et al. | |
| 5,660,175 A * | 8/1997 | Dayal | 128/207.15 |
| 5,665,052 A * | 9/1997 | Bullard | 600/194 |
| 5,694,929 A | 12/1997 | Christopher | |
| 5,842,973 A * | 12/1998 | Bullard | 600/194 |
| 5,913,816 A | 6/1999 | Sanders et al. | |
| 5,921,917 A | 7/1999 | Barthel et al. | |
| 5,945,446 A * | 8/1999 | Laub | 514/456 |
| 5,964,217 A | 10/1999 | Christopher | |
| 6,142,144 A | 11/2000 | Pacey | |
| 6,189,533 B1 | 2/2001 | Simon et al. | |
| 6,196,225 B1 | 3/2001 | Allgeyer | |
| 6,299,622 B1 * | 10/2001 | Snow et al. | 606/159 |
| 6,443,156 B1 * | 9/2002 | Niklason et al. | 128/207.14 |
| 6,520,183 B2 | 2/2003 | Amar | |
| 6,543,446 B1 | 4/2003 | Christopher | |
| 6,550,475 B1 * | 4/2003 | Oldfield | 128/200.26 |
| 6,568,388 B2 | 5/2003 | Christopher | |
| 6,629,924 B2 | 10/2003 | Aydelotte | |
| 6,631,713 B1 | 10/2003 | Christopher | |
| 6,672,305 B2 | 1/2004 | Parker | |
| 6,698,428 B2 * | 3/2004 | Brain | 128/207.14 |
| 6,820,618 B2 | 11/2004 | Banner et al. | |
| 6,849,042 B2 | 2/2005 | Christopher | |
| 6,860,264 B2 * | 3/2005 | Christopher | 128/200.26 |
| 6,923,176 B2 * | 8/2005 | Ranzinger | 128/200.26 |
| 6,929,600 B2 | 8/2005 | Hill | |
| 7,052,456 B2 | 5/2006 | Simon | |
| 7,121,280 B2 * | 10/2006 | Kyle, Jr. | 128/207.14 |
| 7,921,847 B2 * | 4/2011 | Totz | 128/207.15 |
| 2002/0007110 A1 * | 1/2002 | Irion | 600/170 |
| 2004/0111069 A1 * | 6/2004 | Schaaf et al. | 604/284 |
| 2005/0039754 A1 * | 2/2005 | Simon | 128/207.14 |
| 2005/0159645 A1 * | 7/2005 | Bertolero et al. | 600/116 |
| 2006/0025650 A1 | 2/2006 | Gavriely | |
| 2006/0122460 A1 | 6/2006 | Kamali | |
| 2007/0137651 A1 | 6/2007 | Glassenberg et al. | |
| 2008/0039715 A1 | 2/2008 | Wilson et al. | |
| 2008/0312497 A1 * | 12/2008 | Elmouelhi et al. | 600/104 |
| 2009/0203962 A1 * | 8/2009 | Miller et al. | 600/109 |
| 2010/0030057 A1 | 2/2010 | Gavriely | |
| 2012/0004544 A9 * | 1/2012 | Saadat et al. | 600/433 |
| 2012/0024292 A1 | 2/2012 | Sandmore et al. | |
| 2012/0259173 A1 | 10/2012 | Waldron et al. | |
| 2012/0302833 A1 * | 11/2012 | Hayman et al. | 600/120 |

OTHER PUBLICATIONS

U.S. Appl. No. 13/222,645, filed Aug. 31, 2011, Sarah Hayman.

Salem, MR, "Verification of Endotracheal Tube Placement", Anesthesiology Clinics of North America, vol. 19(4); pp. 831-839 (Dec. 1, 2001).

Kristensen, MS, "The Parker Flex-Tip Tube versus a Standard Tube for Fiberoptic Orotracheal Intubation", Anesthesiology, vol. 98, No. 2, Feb. 2003.

Kohase, H. et al., "Endotracheal Intubation Device with a Charge Couple Device Camera", Anesth. Analg. 2003; 96:43-4.

Makino, H. et al., "The Effects of Traceal Tube Tip Design and Tube Thickness on Laryngeal Pass Ability During Oral Tube Exchange with an Introducer", Anesth Analog 2003; 97:285-8.

Sehata, H. et al., "Tracheal intubation using a new CCD camera-equipped device: a report of two cases with a difficult intubation", Acta Anaesthesiologica Scandinavica, vol. 49, No. 8, Sep. 2005, pp. 1218-1220(3).

Kaplan, MB et al., "Seeing is believing: the importance of video laryngoscopy in teaching and in managing the difficult airway", Surg. Endosc. Apr. 2006;20 Suppl 2:S479-83. Epub Mar. 16, 2006.

Arndt Endobronchial Blocker, Cook Medical, http://www.cookmedical.com/cc/familyListingAction.do?family=Endobronchial+Blockers, Copyright 2011.

Cohen Endobronchial Blocker, Cook Medical, http://www.cookmedical.com/cc/familyListingAction.do?family=Endobronchial+Blockers, Copyright 2011.

Portex, Endobronchial Double Lumen, Smiths-Medical, http://www.smiths-medical.com/catalog/endotracheal-tubes, Copyright 2011.

Portex, Endobronchial Double Lumen, Smiths-Medical, http://www.smiths-medical.com/catalog/endotracheal-tub, Copyright 2011.

Respiratory Care—http://www.smiths-medical.com/markets/respiratory-care/ (Apr. 1, 2010).

* cited by examiner

US 8,998,798 B2

MULTI-LUMEN TRACHEAL TUBE WITH VISUALIZATION DEVICE

BACKGROUND

The present disclosure relates generally to medical devices and, more particularly, to multi-lumen tracheal tubes that may accommodate an integral visualization device, such as a camera.

This section is intended to introduce the reader to various aspects of art that may be related to various aspects of the present disclosure, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

In the course of treating a patient, a tracheal tube (e.g. endotracheal, endobronchial, nasotracheal, or transtracheal device) may be used to control the flow of gases into the trachea of a patient. Often, a seal between the outside of the tube and the interior wall of the tracheal lumen is required, allowing for generation of positive intrathoracic pressure distal to the seal and prevention of ingress of solid or liquid matter into the lungs from proximal to the seal.

Depending on the clinical condition of the patient, a tracheal tube may be inserted that is capable of ventilating one lung to the exclusion or independently of the other. For example, during thoracic surgery, surgeons may wish to isolate and perform surgery on an affected lung while simultaneously ventilating the healthy lung in order to optimize the surgical field and/or avoid cross-contamination.

Endobronchial tubes that allow independent control of each lung through dual lumens are typically used for this purpose. One lumen is opened to ambient pressure to isolate the desired lung, while respiratory and anesthetic gases are delivered via positive pressure ventilation through the other lumen. Placement of an endobronchial tube not only requires corroboration of correct insertion and positioning within the trachea, but also additional corroboration of correct insertion and positioning within the desired main-stem bronchus. Placement must be reassessed frequently after patient position changes for surgical indications (e.g. lateral decubitus positioning), during surgical manipulations and after tube manipulations. This corroboration of placement requires bronchoscopic evaluation through the tracheal and/or bronchial lumen to visualize whether the bronchial lumen has been correctly cannulated and whether the tip of the bronchial lumen is correctly positioned. However, bronchoscopy is time consuming, can interrupt ventilation, and requires additional skills on the part of the provider. In addition, bronchoscopes are bulky, expensive, prone to damage, and difficult to operate within the relatively small diameter of the bronchial lumen.

BRIEF DESCRIPTION OF THE DRAWINGS

Advantages of the disclosed techniques may become apparent upon reading the following detailed description and upon reference to the drawings in which.

DETAILED DESCRIPTION OF SPECIFIC EMBODIMENTS

Figure 1:
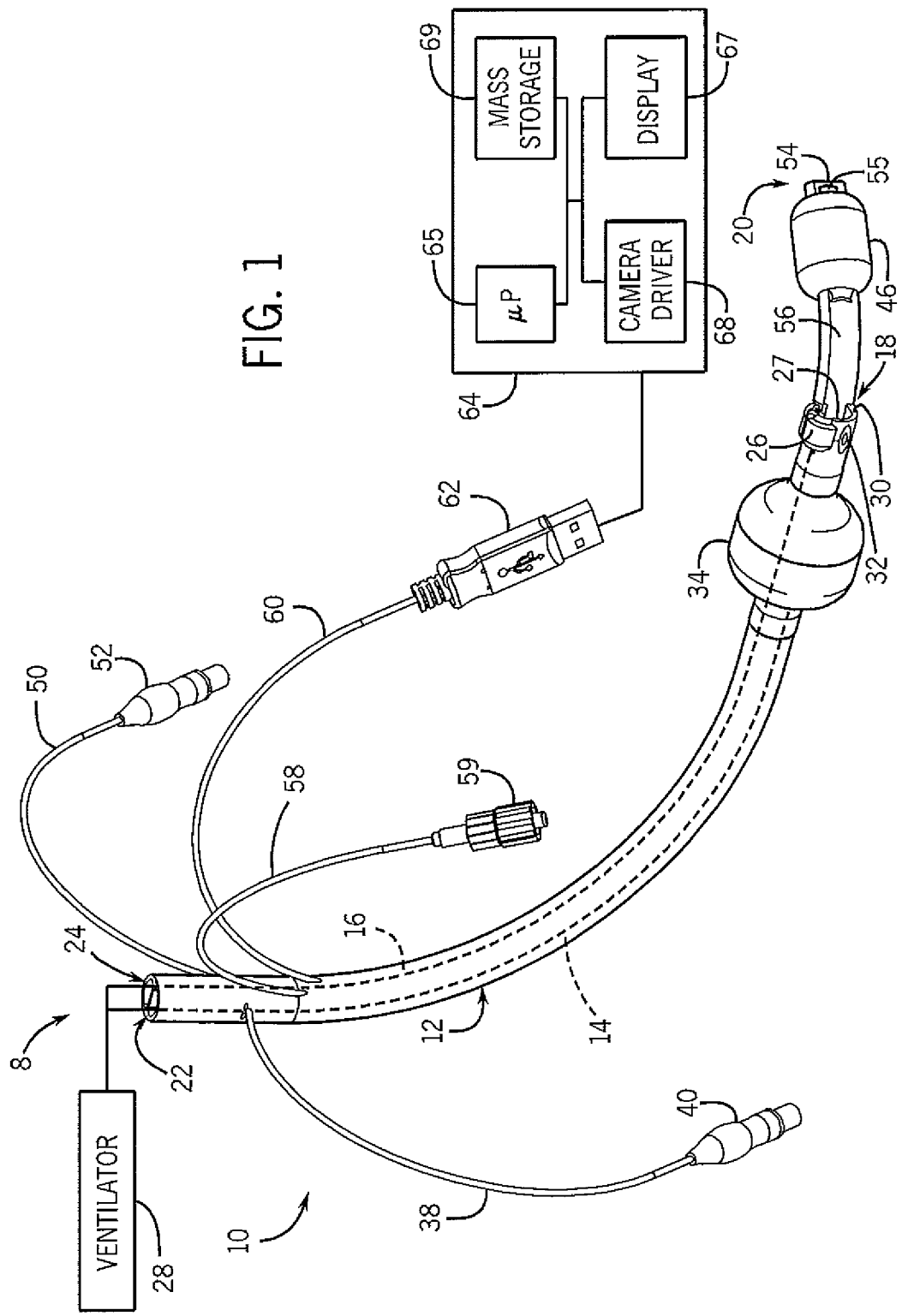
FIG. 1 is an elevational view of an endobronchial tube including a visualization device in accordance with aspects of the present disclosure.

One or more specific embodiments of the present techniques will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

As described in detail below, embodiments of a tracheal tube having an integral visualization apparatus, e.g., a camera, are provided herein. In a particular embodiment, the tracheal tube may be an endobronchial tube. Endobronchial tubes are double-lumen tracheal tubes that facilitate an airtight seal in the trachea and one stem of a patient bronchus to allow independent ventilation of one lung. Generally, an endobronchial tube includes two tubes of unequal length that are attached. One tube terminates within the tracheal airway space, i.e., the shorter tube has a distal end at a location similar to a typical endotracheal tube. The other, longer, tube is configured to extend past the shorter tube and into a left or right bronchial stem. Both tubes define a passageway for transferring fluids to and from a patient.

While the total diameter of an endobronchial tube may be larger than that of a single lumen endotracheal tube, the diameter of each individual lumen of the endobronchial tube is relatively smaller than that of a single lumen endotracheal tube. Such a shift in diameter may be challenging for physicians during placement of an endobronchial tube. Because the endobronchial tube involves not only correct intubation within the trachea but also correct placement of the bronchial lumen with a left or right bronchial stem, physicians may use visualizing devices such as bronchoscopes to aid in the placement of the bronchial tube. However, commercial bronchoscopes are generally sized and shaped to be used in conjunction with the relatively larger lumen of a single-lumen endotracheal tube. As such, the bronchoscopes may not fit easily within either lumen of a double-lumen endobronchial tube.

The tracheal tubes provided herein include built-in visualization devices that preferably 1. facilitate proper placement of the tube through the vocal cords, into the trachea; 2. facilitate subsequent proper placement into the appropriate mainstem bronchus; 3. facilitate intermittent or continuous corroboration of positioning within the mainstem bronchus via visual assessment; and/or 4. facilitate intermittent or continuous evaluation of a patient's medical condition via assessment of changes within the mainstem bronchus or trachea (e.g. hemorrhage, accumulation of secretions, lung volume expansion, etc). These devices may preferably accomplish these endpoints with minimum to no impact on inner diameter of the tube lumens, no significant change in resistance to gas flow through the tube lumens, no interruption or reduction of fresh gas ventilation, and no requirement for use of a bronchoscope to assess tube placement or position. In addition, because endobronchial tubes are specifically designed for the anatomy of the right or left-mainstem bronchus, the built-in visualization devices are tailored to address specific challenges presented by the unique anatomic differences (e.g. right upper lobe occlusion).

The tracheal tubes as provided herein are preferably disposable rather than reusable, capable of providing differential mechanical ventilation to either or both lungs, and capable of supporting all other functions of standard endotracheal tubes (e.g. sealing, positive pressure generation, suctioning, irrigation, drug instillation, etc). The tracheal tubes may further be used in conjunction with acceptable auxiliary airway devices such as (e.g. heat and humidity conservers, mechanical ventilators, humidifiers, closed suction systems, scavengers, capnometers, oxygen analyzers, mass spectrometers, PEEP/CPAP devices, etc).

Furthermore, although the embodiments of the present disclosure illustrated and described herein are discussed in the context of tracheal tubes such as endobronchial tubes, it should be noted that presently contemplated embodiments may include a visualization device associated with any of a variety of suitable airway devices. For example, a visualization device as provided herein may be associated with a single-lumen tube, tracheostomy tube, a Broncho-Cath™ tube, a specialty tube, or any other airway device with a main ventilation lumen. Indeed, any device with a ventilation lumen designed for use in an airway of a patient may include a visualization device (e.g., a camera disposed on or within a collar). Furthermore, as used herein, the term "tracheal tube" may include an endotracheal tube, a tracheostomy tube, a Broncho-Cath™ tube, a bronchoblocking tube, a specialty tube, or any other suitable airway device.

Turning now to the drawings, FIG. 1 is a perspective view of a system 8 including an exemplary tracheal tube 10 configured to be placed in a patient bronchial stem in accordance with aspects of the present disclosure. The tracheal tube 10 includes a central tubular body 12 with a tracheal ventilation lumen 14 and a bronchial ventilation lumen 16. The tracheal lumen terminates at a tracheal lumen distal end 18 while the bronchial lumen terminates in a bronchial lumen distal end 20. Furthermore, the tracheal tube 10 may include a tracheal lumen proximal end 22 and a bronchial lumen proximal end 24. As shown, the tracheal ventilation lumen 14 and a bronchial ventilation lumen 16 may be attached to one another over a portion of the tubular body 12 and may separate at their respective proximal ends 22, 24 and distal ends 18, 20. The tube 10 may include a visualization device 26 associated with one or both of the tracheal ventilation lumen 14 and the bronchial ventilation lumen 16. Over the portion of the tubular body 12 in which the tracheal ventilation lumen 14 and a bronchial ventilation lumen 16 are attached, the tubular body 12 may include a separating wall 27.

The tracheal lumen proximal end 22 and a bronchial lumen proximal end 24 may be outfitted with separate connectors that may be attached to a ventilation device 28 during operation that may include a suitable controller (e.g., a processor-based control system) so that a clinician may direct airflow to and from both the tracheal ventilation lumen 14 and bronchial ventilation lumen 16. In other embodiments, either tracheal ventilation lumen 14 or the bronchial ventilation lumen 16 may be blocked or otherwise closed such that only one of the two lumens of the tracheal tube 10 is operational.

The tracheal lumen distal end 18 of ventilation lumen 14 terminates in an opening 30 and may be placed in a patient trachea during operation to maintain airflow to and from the patient's lungs. A Murphy's eye 32 may be optionally present and located on the ventilation lumen 14 opposite the opening 30 to prevent airway occlusion when the tracheal tube assembly 10 is improperly placed within the patient's trachea. As illustrated, a tracheal cuff 34 may encircle the tubular body 12 and be inflated to seal against the walls of a body cavity (e.g., a trachea). The cuff 34 may be inflated via an inflation lumen terminating in an inflation tube 38 connected to an inflation pilot balloon and valve assembly 40. Additionally, it should be noted that the cuff 34 may be any suitable cuff, such as a tapered cuff, a non-tapered cuff, and so forth. The tracheal ventilation lumen 14 may also include a suction lumen (not shown) that extends from a location on the tracheal tube 10 positioned outside the body when in use to a location on the tubular body 12 that terminates in a port located proximally to cuff 34 through which secretions may be aspirated. Bronchial ventilation lumen 16 is longer than tracheal ventilation lumen 14 and includes a distal end 20 that extends past the tracheal lumen distal end 18. The bronchial ventilation lumen 16 may include a bronchial inflation cuff 46 that is configured to seal against the walls of a patient's bronchus. The cuff 46 may be inflated via an inflation lumen terminating in an inflation tube 50 connected to an inflation pilot balloon and valve assembly 52.

The tubular body 12 and the cuffs 34 and 46 may be formed from materials having desirable mechanical properties (e.g., puncture resistance, pin hole resistance, tensile strength, and so forth) and desirable chemical properties (e.g., biocompatibility). Further, in one embodiment, the walls of the cuff 34 or cuff 46 may be made of a polyurethane (e.g., Dow Pellethane® 2363-80A) having suitable mechanical and chemical properties. In other embodiments, the walls of the cuff 34 or cuff 46 may be made of silicone or a suitable polyvinyl chloride (PVC). In certain embodiments, the cuff 34 or cuff 46 may be generally sized and shaped as a high volume, low pressure cuff that may be designed to be inflated to pressures between about 15 cm $H_2O$ and 30 cm $H_2O$. Further, bronchial cuff 46 may be a different color or include other identifying markings that allow a user to differentiate between the tracheal cuff 34 and the bronchial cuff 46. In addition, to assist in proper placement of the tube 10, x-ray visible markings 56 may be placed at any appropriate location. For example, the markings 56 may outline a bronchial distal opening 54 or a side eye 55.

In addition, portions of the visualization device 26 may be formed from the same material or different materials as the tube 10. Generally, the visualization device 26 may be formed from biocompatible polymers and other nonreactive materials. It should also be understood that certain portions of the visualization device may be coated with antimicrobial materials to prevent bacterial adhesion or fouling. In embodiments in which camera lenses are coated, the antimicrobial coatings may be selected to minimize interference with image acquisition. The visualization device 26 may be adhered to or fastened to the tubular body 12 by any suitable process. For example, the visualization device 26 may be embedded in or adhered (e.g., welded) to tubular body 12. In addition, coupling to the tube 10 may be assisted by threading cables or other attachments into lumens formed in the tubular body 12. In particular embodiments, the tubular body 12 may include notches or recesses within the walls that accommodate the visualization device 26 and that do not impact the inner diameter of the ventilation lumens. Insofar as these recesses may be structurally less rigid than the rest of the tubular body 12, application of the visualization device 26 may restore rigidity to the relatively thinner recesses.

In one embodiment, the tube 10 may also include a fluid delivery lumen 58 in communication with the visualization device 26. The fluid delivery lumen 58 may terminate in a distal coupler 59 that is sized and shaped to connect to a fluid source (e.g., a saline reservoir, a syringe). A portion of the fluid delivery lumen 58 may be formed within a wall of the tube 10. The fluid delivery lumen 58 may be configured to flush or clear mucus buildup on the visualization device 26. The tube 10 may also include a cable 60 coupled to the visualization device 26. The cable 60 may run along or within (e.g., in a dedicated lumen) the tubular body 12. The cable 60 may terminate in an electrical connector 62.

The system may also include a monitor 64 that may be configured to implement embodiments of the present disclosure and may be coupled to the visualization device 26 via connector 62 (e.g., a USB connector) and cable 60. It should be understood that the monitor 64 may be a stand-alone device or may, in embodiments, be integrated into a single device with, for example, the ventilator 28. The monitor 64 may include processing circuitry, such as a microprocessor 65 coupled to an internal bus and a display 67. In an embodiment, the monitor 64 may be configured to communicate with the tube via connector 62, to obtain signals from the visualization device 26. The information may then be stored in mass storage device 69, such as RAM, PROM, optical storage devices, flash memory devices, hardware storage devices, magnetic storage devices, or any suitable computer-readable storage medium. The information may be accessed and operated upon according to microprocessor 65 instructions. The monitor 64 may be configured to provide indications of tube placement within the trachea, such as an audio, visual or other indication, or may be configured to communicate the information to another device, such as the ventilator 28. In certain embodiments, the monitor 64 may also provide camera drive signals (including a drive signal to any associated light sources) to the visualization device 26 via camera driver 68. The drive signal from the camera driver 68 to the camera and light sources may be adjusted to reduce heating and power consumption of the visualization device 26. For example, the camera driver 68 may drive the camera continuously or intermittently or only at designated times during intubation.

Figure 2:
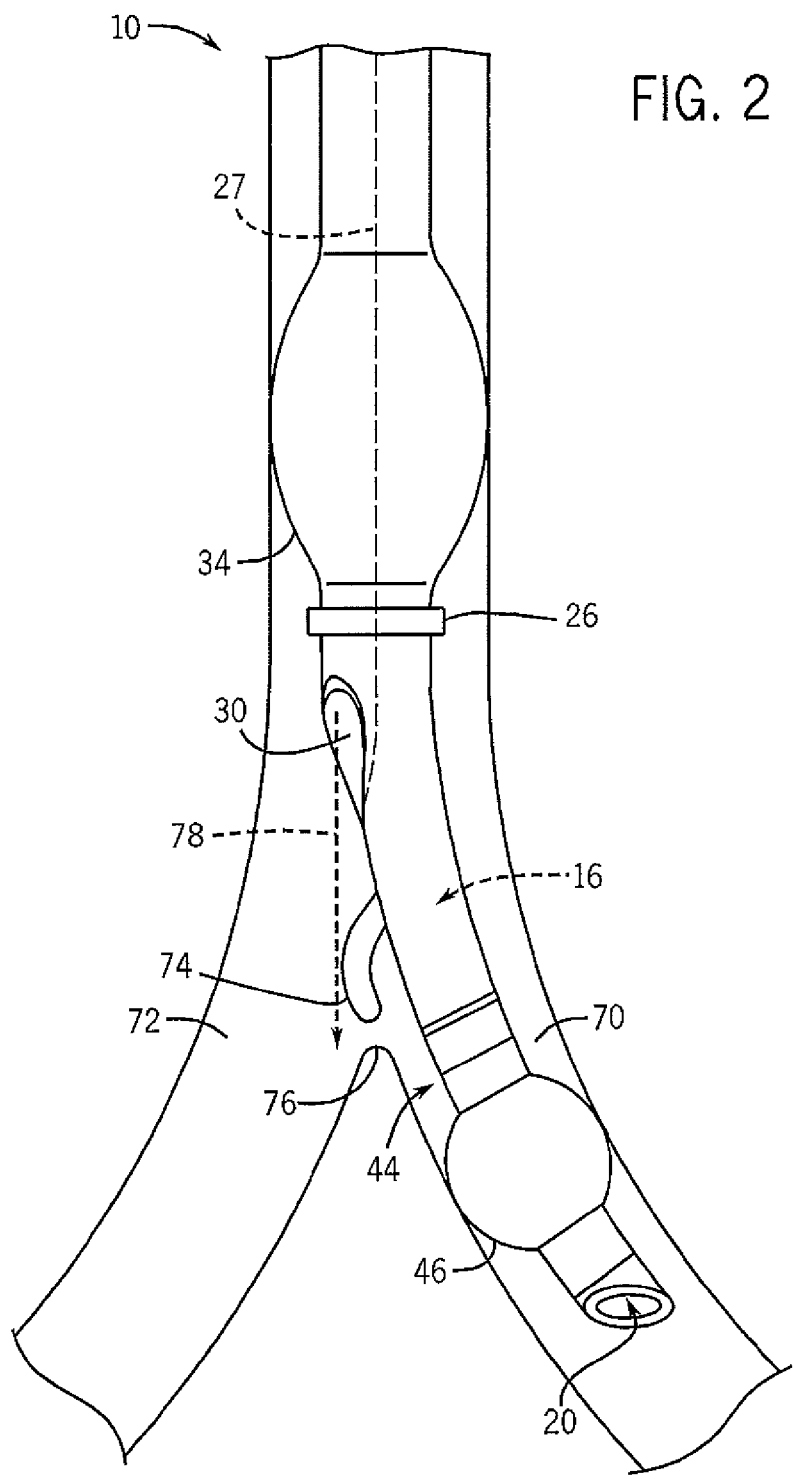
FIG. 2 is a perspective view of an exemplary endobronchial tube positioned within the left bronchus of a patient.

During operation, a tracheal tube 10 is inserted into the trachea of a patient and positioned within the left or right bronchial stem and the tracheal cuff 34 and bronchial cuff 46 are inflated to isolate the appropriate airway structures. In certain embodiments, a tracheal tube 10 may be configured to be positioned within a left bronchial stem 70, as shown in FIG. 2. In such an embodiment, the tube 10 may have particular features that assist in positioning the distal portion 44 and the bronchial cuff 46. For example, relative to the right bronchial stein 72, the left bronchial stein is relatively curved. Accordingly, the distal portion 44 may be curved in a similar manner. Further, the tube 10 optionally may include a protrusion 74 (e.g., carinal hook) to help position the tube 10 relative to the patient's carina 76.

After insertion of the tracheal tube 10, the visualization device 26 may be positioned so that its field of view is generally oriented in a distal direction (indicated by arrow 78). Such an orientation may allow viewing of the carina 76 or one or both of the left bronchial stem 70 or the right bronchial stem 72, which in turn may allow information about the placement of the tube 10 to be determined. In contrast to a bronchoscope, which is removed after the initial insertion of the tracheal tube 10, the visualization device 26 may be fixedly attached to the tracheal tube (e.g., via one or more of adhesion, heat welding, mechanical fasteners) so that information about tube placement may be collected throughout the intubation period. The visualization device 26 as depicted is associated with a distal region 18 of the tracheal ventilation lumen 14 such that the visualization device partially surrounds the lumen 14. In other embodiments, the visualization device may be located more distally on the tube 10. Further, additional visualization devices may be located on the tube 10 as appropriate. In other embodiments in which the visualization device 26 is associated with a single-lumen tube, the visualization device 26 may be located below or on the distal shoulder of the cuff (e.g., in a distal region of a single-lumen tube).

Figure 3:
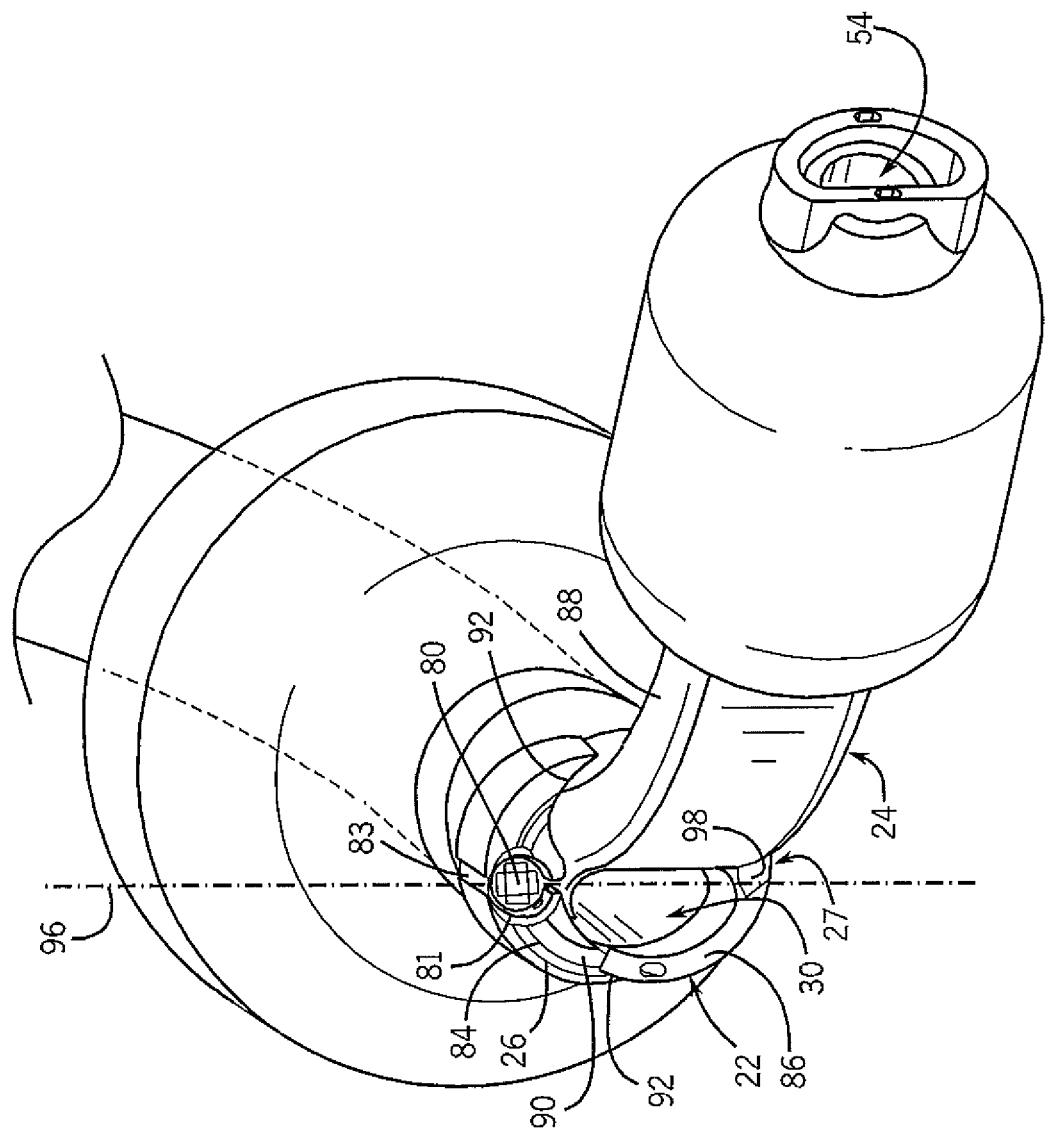
FIG. 3 is a bottom view of a visualization device associated with an endobronchial tube.

FIG. 3 illustrates a bottom view of an exemplary visualization device 26 associated with the tracheal tube 10. As shown, the visualization device 26 may include a camera 80 or other image gathering component that is suitably sized and shaped to be incorporated into the visualization device 26, e.g., a CMOS chip camera. Other suitable image gathering components may include pixel arrays. The camera 80 may be associated with one or more light sources 81 (e.g., light emitting diodes or fiber optic light sources). Supporting circuitry for the camera 80 and light sources 81 may be provided as part of a module or unit 83 that may be incorporated within the housing 84 of the visualization device. Connecting leads from the unit 83, including any light pipes for light sources 81, that extend to cable 60 may be positioned in dedicated lumens formed within the tubular body 12. Further, the supporting circuitry may be disposed on a conventional circuit board or may be disposed on a printed circuit board.

As noted, the visualization device 26 may be affixed to the tubular body 12. In the depicted embodiment, a portion 90 of the housing 84 is embedded within a tracheal ventilation lumen wall 86 and a bronchial ventilation lumen wall 88. The embedded portion 90 is suitably sized and shaped to be embedded within or, in certain embodiments, form a portion of the tubular body 12. For example, the curvature of the housing 84 may be selected to match the curvature of one or both of the ventilations lumens 14 and 16. Extending wings 92 of the housing 84 may provide additional surface area for fixing the visualization device 26 to the tubular body 12.

The housing 84 may be any suitable size or shape to facilitate coupling to the tube 10. For example, the housing 84 may be an annulus, a partial annulus, a collar, or a saddle shape. The housing 84 and other portions of the visualization device 26 may be formed to reduce the profile that extends away from the tubular body 12 because it is desirable to limit the outer diameter of the tube 10, including any associated structures. In certain embodiments, the visualization device protrudes less than 5 mm, 4 mm, 3 mm, 2 mm, or 1 mm away from the tubular body 12, e.g., along axis 96 that is substantially orthogonal to the flow path of the tracheal ventilation lumen 14. In addition, the housing 84 may be formed so that more than 50% of the total volume of the visualization device 26 is embedded within or forms a portion of the tubular body 12. To that end, the supporting circuitry for image collection may be partially or completely disposed within the relatively thicker embedded portion 90. In particular embodiments, the visualization device 26 may be affixed to the tube 10 at certain portions of the tubular body 12 that are relatively thicker and may provide better support for the weight and volume of the visualization device 26. For example, the junction 98 of the separating wall 27, tracheal ventilation lumen wall 86, and the bronchial ventilation lumen wall 88 may be the thickest point along the tracheal tube 10. As such, the camera 80 of the visualization device 26 may be circumferentially aligned with junction 98. Such alignment may also facilitate improved image acquisition with regard to certain anatomical features, such as the carina 76. In particular embodiments, the camera 80 may be circumferentially aligned within 10 degrees, within 15 degrees, or within 30 degrees of junction 98.

In particular embodiments, it may be advantageous to align the camera 80 anterially. For example, the camera 80 may be positioned on the portion of the tubular body 12 that touches the anterior wall of the trachea when inserted. In particular, for a left-sided or a right-sided bronchial tube, anterior alignment may be advantageous In addition, it may be advantageous to affix the visualization device 26 on the bronchial ventilation lumen 16 below the tracheal lumen distal opening 30 but proximal to the carina 76.

Figure 4:
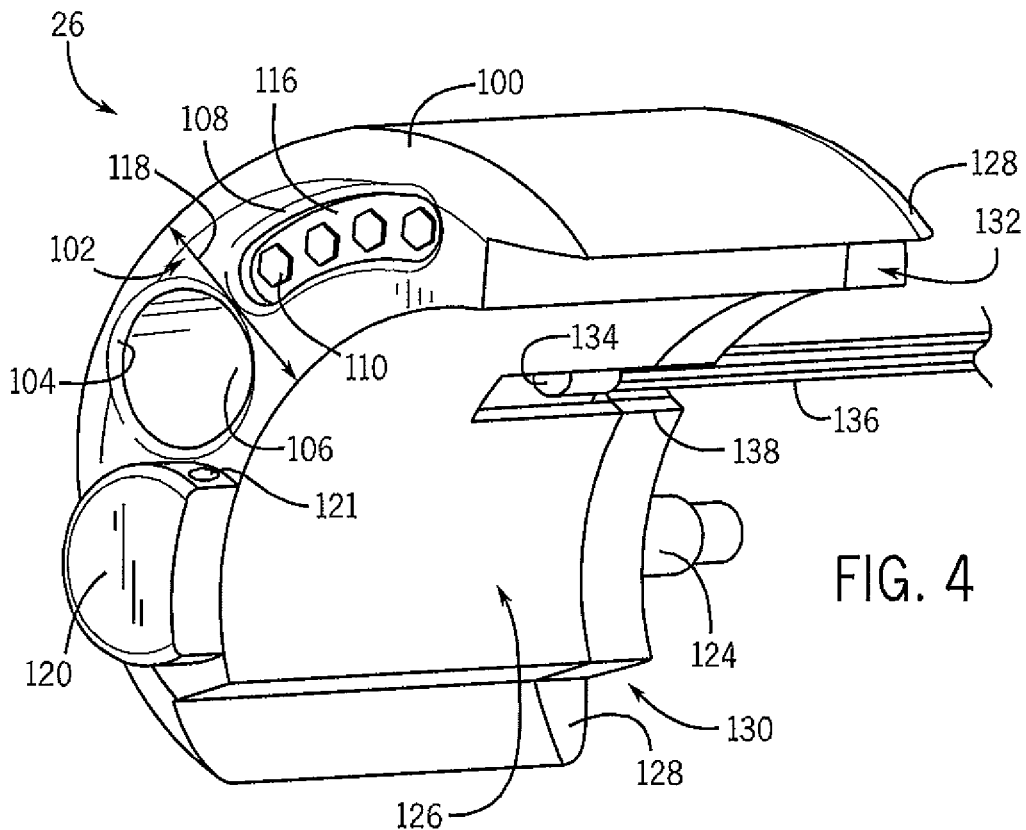
FIG. 4 is partial perspective view of a visualization device that may be used in conjunction with a tracheal tube.

FIG. 4 is a perspective view of an exemplary visualization device 26 with a partially annular housing 100. A distal surface of the visualization device forms a bore, recess, or aperture 104 that accommodates a camera assembly 106 (e.g., a lens and/or other image gathering structures). As depicted, the distal surface 102 also includes an aperture 108 sized to accommodate one or more light sources 110. As depicted, the light sources 110 may be associated with a backing or housing 116, which in turn may be part of a circuitry unit 134 containing the supporting circuitry for the camera assembly 106. The length 118 of the distal surface 102 may be selected so that the profile of the housing is minimized, and may include a portion that is embedded in the tracheal wall and a portion that protrudes.

In certain embodiments, the distal surface 102 may include a fluid delivery assembly 120 that includes an opening 121 angled towards the camera assembly 106. In particular embodiments, the fluid delivery assembly 120 may include multiple openings 121 so that fluid (e.g., water, saline, etc.) may be directed at camera lens as well as associated light sources. In such embodiments, the positioning and angle of the openings 121 may be selected to facilitate cleaning of the desired object. The fluid delivery assembly is in fluid communication with fluid coupler 124, which in turn may be coupled to a fluid delivery lumen 58 (see FIG. 1) that extends along the tubular body 12 and terminates in an opening proximate to the visualization device 26. The fluid coupler 124 may be sized and shaped to facilitate insertion into the distal opening in the fluid delivery lumen 58. Accordingly, the fluid coupler 124 may be inserted into the opening in the fluid delivery lumen 58 as part of coupling the visualization device 26 to the tube 10. In particular embodiments, the delivery assembly 120 may be a separate component that is coupled to or otherwise associated with the visualization device 26.

Figure 5:
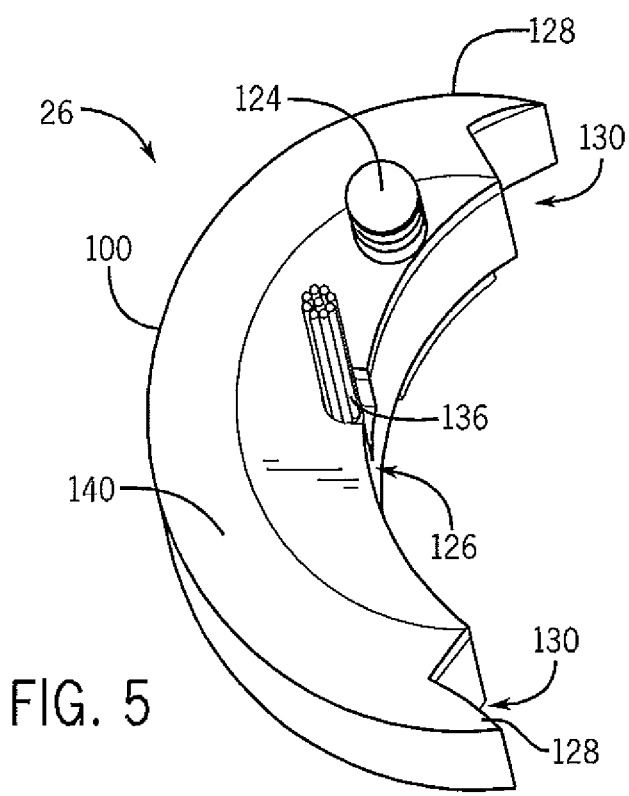
FIG. 5 is top view of the visualization device of FIG. 4.

The interior face 126 of the housing 100 may be curved to follow the curvature and circumference of the ventilation lumens 14 or 16, particularly in embodiments in which the interior face 126 is embedded in the tubular body 12 and forms a portion of one or both of the ventilation lumens 14 and 16. Extending portions 128 that wrap around the exterior surface of the tube wall 12 are formed about notches 130 that separate the extending portions 128 from the embedded portion 132. Cable 136 (e.g., a multi-wire cable) extends from the circuitry unit 134 through notch 138 in the housing 100. As shown in top view in FIG. 5, the cable 136 and the fluid delivery coupler 124 extend from the proximal surface 140 of the visualization device 26. The cable 136 may be routed through a dedicated lumen in the tubular body 12 or may be embedded in or otherwise associated with the tube before terminating in a portion proximal to the tube and a connector 28. The cable 136 may also be printed on or within the tubular body 12. In such embodiments, leads or wires from device 26 and the cable 60 may be electrically coupled to the printed wires.

Figure 6:
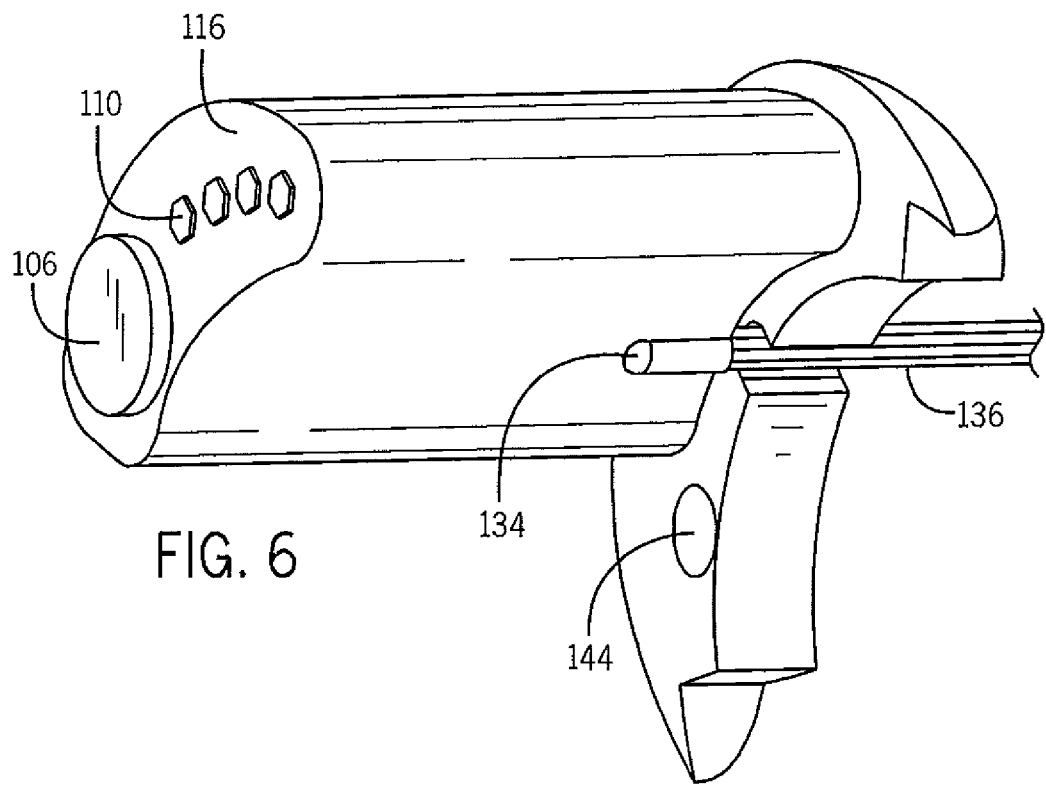
FIG. 6 is cutaway view of the electronic components of the visualization device of FIG. 4.

FIG. 6 is a component view of the circuitry unit 134 coupled to a proximal housing face 144 that forms the proximal surface 140 of the housing 110. It is contemplated that, in particular embodiments, providing the camera assembly 106 and/or light sources 110 as a unitary assembly with circuitry unit 134 may streamline manufacturing of the visualization device 26. The circuitry unit 134 may be configured in any suitable manner. For example, the position of the light sources 110 and the camera assembly 106 may be selected to facilitate viewing of certain anatomical features. In certain embodiments, the light sources 110 may be disposed symmetrically or asymmetrically about the camera assembly 106.

Figure 7:
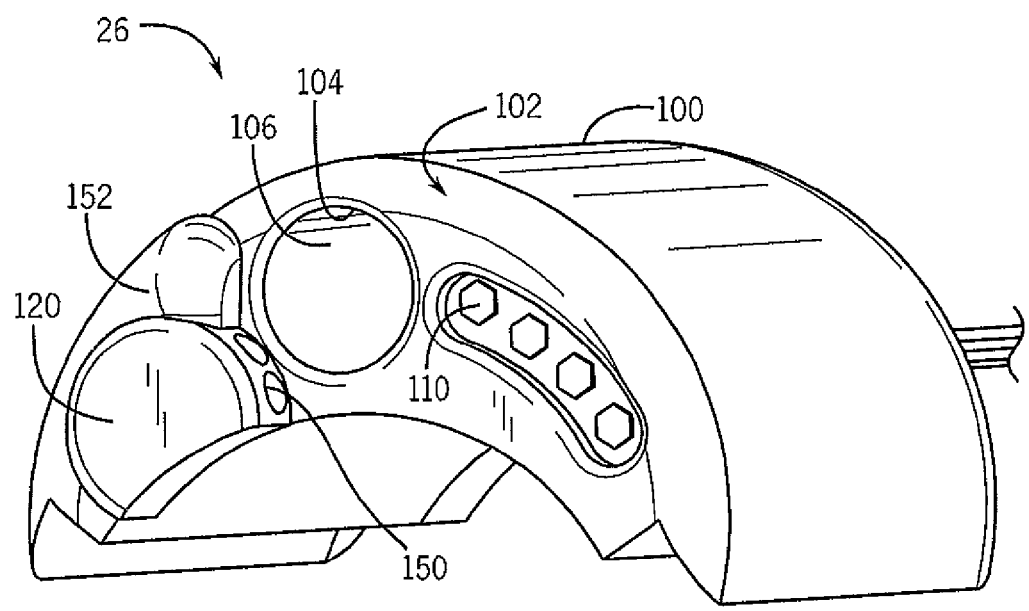
FIG. 7 is a partial perspective view of a visualization device that may be used in conjunction with a tracheal tube.

FIG. 7 is a perspective view of an alternative arrangement of a visualization device 26. In the depicted embodiment, the housing 100 includes a guard 152 disposed proximate to the fluid delivery assembly 120. The guard 152 functions to smooth the exposed surfaces of the fluid delivery assembly 120. In addition, the guard 152 may direct the flow of fluid from openings 150 in a desired direction (e.g., towards the camera assembly 106). The guard 152 may be molded or otherwise formed in the housing 100

Figure 8:
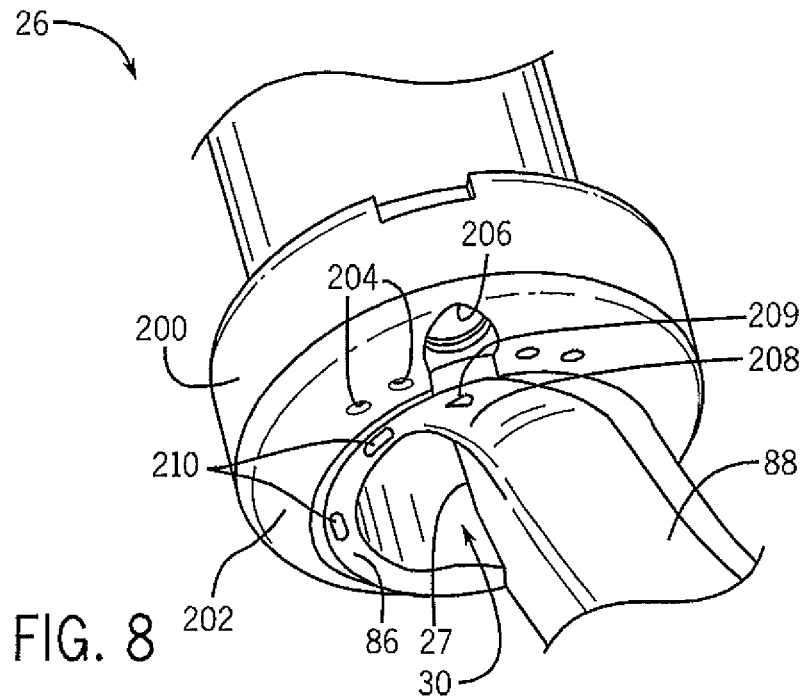
FIG. 8 is a partial perspective view of a visualization device associated with an endobronchial tube.

FIG. 8 is perspective view of an annular visualization device 26. It should be understood that the visualization devices 26 may be annular or partially annular (e.g., saddle-shaped). In certain embodiments, a saddle-shaped visualization device 26 may protrude less relative to an annular shape. The housing 200 has a distal surface 202 that includes bores 204 for accommodating one or more light sources and a bore 206 to accommodate a camera assembly. The visualization device is positioned at the distal region 18 and vertically aligned with the location of the opening 30. In particular embodiments, the bore 206 for the camera assembly is positioned to be rotationally aligned with a junction point 208 of the dividing wall 27, tracheal ventilation lumen wall 86, and the bronchial ventilation lumen wall 88. In addition, the bore 206 is aligned with a lumen 209 formed in the dividing wall 27. The lumen 209 may be coupled to the cable of the visualization device 26 through a notch or opening located near the proximal surface of the visualization device 26. The tracheal ventilation lumen may also feature additional lumens 210 that may couple to other assemblies (e.g., fluid delivery assemblies). Depending on the rotational alignment of the visualization device 26, the lumens 210 may be within the tracheal ventilation lumen wall 86, and the bronchial ventilation lumen wall 88.

Figure 9:
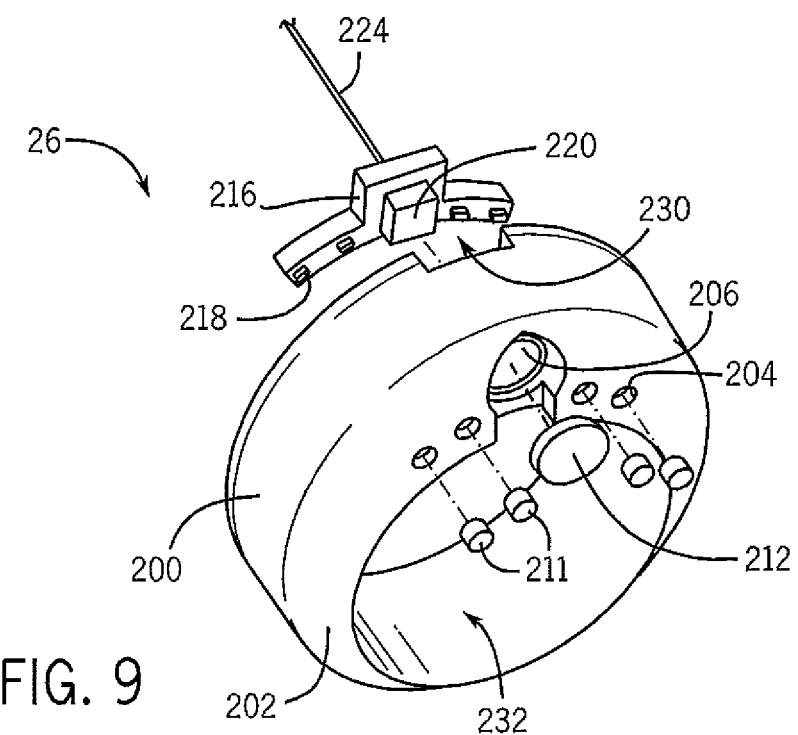
FIG. 9 is an exploded view of the visualization device of FIG. 8.

FIG. 9 is an exploded view of the visualization device of FIG. 8. The visualization device includes windows or covers 211 and 212 sized to be used with light source bores 204 and camera bore 206. The camera assembly 216 is shown as fitting within a designated notch 230 in the housing 200. The bores 204 and 206 are positioned to align with light sources 218 and camera 220, respectively. Cable 224 extends proximally from the camera assembly 216. The bore 232 through the center of the annular housing 200 is sized to be approximately equal to or slightly larger than a tube outer diameter at the attachment point. In other embodiments, multiple light sources 218 or the light sources 218 and the camera 220 may be covered by a single appropriately-shaped cover.

Figure 10:
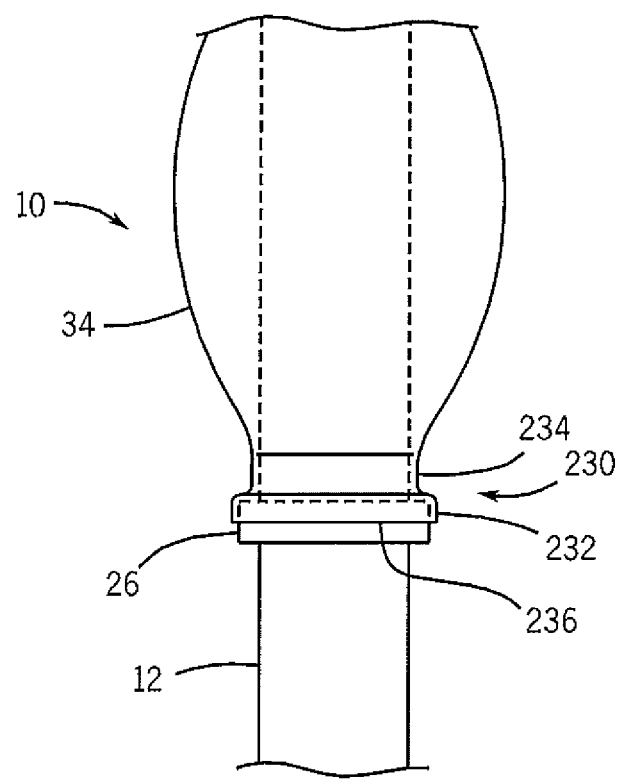
FIG. 10 is a side view of a visualization device coupled to the tube via a cuff shoulder.

FIG. 10 is a side view of the visualization device 26 coupled to the tubular body 12. As noted, the visualization device 26 may be adhered to or otherwise fixedly attached to the tubular body 12. In addition, certain structures associated with the visualization device 26, such as the nozzle 124 or the cable 136, may be embedded within the wall of the tube 10, which may facilitate coupling of the visualization device 26 to the tube 10. As depicted in FIG. 10, the visualization device 26 may be further affixed to the tube 10 via a compression force provided by a distal cuff shoulder 230. It should be understood that adhesives may be used to further affix the distal shoulder 230 to the visualization device 26. In the illustrated embodiment, during manufacturing, at least a portion 232 of the distal shoulder 230 may be pulled over the visualization device 26, leaving a portion 234 of the distal shoulder 230 directly affixed to the tubular body to anchor the cuff 34 and prevent further inflation of the cuff 34 past portion 234. The portion 232 may partially cover the visualization device 26 so that the distal end 236 of the distal shoulder 230 rests on the visualization device 26 and not on the tubular body 12. In addition, any notches or holes in the tubular body 12 for connection to lumens (e.g., fluid delivery lumen 58) or cables (e.g., cable 60) may be positioned on the tubular body 12 in a region under the distal shoulder 230. In certain embodiments, a distal end 236 of the distal shoulder is positioned distally of the visualization device 26 and comes into direct contact with the tubular body 12 so that the visualization device 26 is completely covered by the distal shoulder 230 and anchored proximally and distally. In such embodiments, the material of the cuff 34 may be sufficiently transparent so that the camera and light sources are substantially unaffected by being covered by the distal shoulder region 230. In a particular embodiment, the cuff 34 may be designed with an extended distal shoulder length so that the length of the portion 234 of the distal shoulder directly affixed to the tubular body 12 is substantially unaffected (e.g., such that the total surface area of distal shoulder 230 in contact with the tubular body 12 is about the same relative to implementations in which the visualization device 26 is not positioned under the distal shoulder 230).

Figure 11:
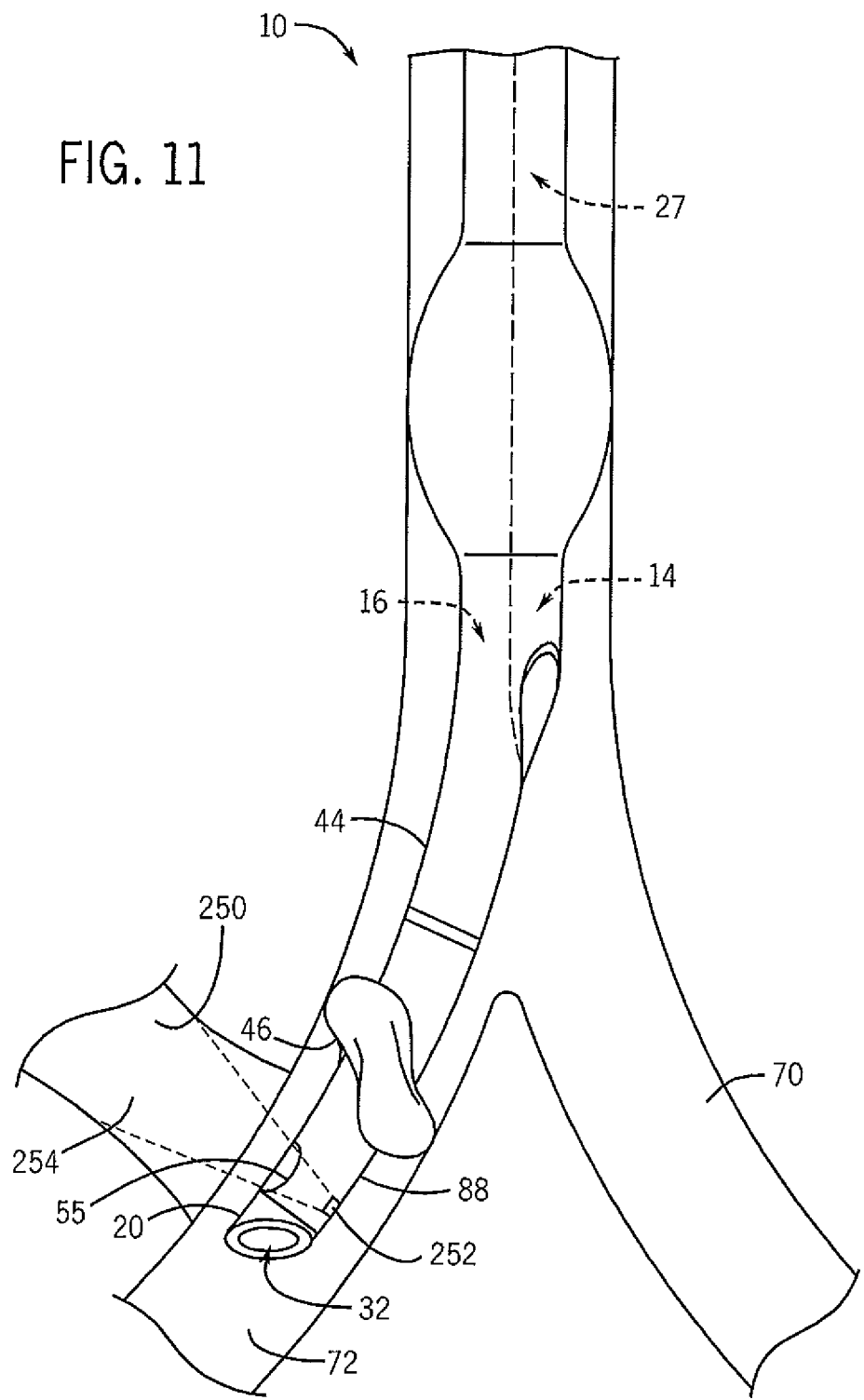
FIG. 11 is a perspective view of an exemplary endobronchial tube positioned within the right bronchus of a patient.

FIG. 11 illustrates a tracheal tube 10 that is configured to be positioned within a right bronchial stem 72. Because the right stein is relatively straighter than the left bronchial stem 70, the distal portion 44 of the tube 10 may have less of a curve. In addition, the bronchial cuff 46 may be shaped, for example with an S-shape, to provide a seal without occluding the right upper lobe. Relative to a left-sided bronchial tube, a right-sided tube presents additional challenges related to the insertion of the tube 10. Proper insertion may involve aligning the distal end 20 of the bronchial ventilation lumen 16 with respect to an upper right bronchus 250. However, because this feature branches off to the side of the right bronchial stem 72, visualization through the distal opening 32 is difficult. Provided herein are tubes 10 that include a camera assembly 252 positioned so that its field of view 254 extends through the side eye or fenestration 55 to permit visualization of the upper right bronchus 250. As depicted, an endobronchial tube may include a camera assembly 252 positioned on the tubular body 12 vertically aligned and circumferentially opposite the side eye 55 (e.g., Murphy eye or fenestration) at the distal end 20 of the bronchial ventilation lumen 16. In particular embodiments, the camera assembly may be at least partially embedded in the tubular body so that inner diameter loss in the bronchial ventilation lumen 16 is minimized. It should be understood that, in addition to the depicted camera assembly 252, the tube 10 may also include additional visualization devices 26, e.g., associated with the distal end 18 of the tracheal ventilation lumen.

While the disclosure may be susceptible to various modifications and alternative forms, specific embodiments have been shown by way of example in the drawings and have been described in detail herein. However, it should be understood that the embodiments provided herein are not intended to be limited to the particular forms disclosed. Rather, the various embodiments may cover all modifications, equivalents, and alternatives falling within the spirit and scope of the disclosure as defined by the following appended claims.

What is claimed is:

1. A tracheal tube, comprising:
   a first ventilation lumen having a first distal end and a first proximal end and configured to be coupled to a ventilator;
   a second ventilation lumen adjacent to the first lumen, the second lumen having a second distal end and a second proximal end configured to be coupled to the ventilator, wherein the second ventilation lumen is longer than the first ventilation, wherein the first and second proximal ends co-terminate, and wherein the second distal end is aligned with an upper bronchus of a patient when inserted;
   an opening in a wall of a distal region of the second ventilation lumen, wherein the opening is proximal to the second distal end; and
   a camera attached to the wall of the second ventilation lumen at a location substantially circumferentially opposite the opening, wherein a field of view of the camera is substantially through the opening.

2. The tracheal tube of claim 1, wherein the camera is disposed within a substantially annular collar.

3. The tracheal tube of claim 1, wherein the tracheal tube comprises a right-stem endobronchial tube.

4. The tracheal tube of claim 1, wherein the camera is embedded in the wall of the second ventilation lumen.

5. The tracheal tube of claim 1, comprising one or more light emitting diodes disposed proximate to the camera.

6. The tracheal tube of claim 1, comprising a first cuff disposed around the first ventilation lumen and the second ventilation lumen, and a second cuff disposed around only the second ventilation lumen.

7. The tracheal tube of claim 6, wherein the camera is below the first cuff and the second cuff.

8. The tracheal tube of claim 6, comprising a first inflation lumen associated with the first cuff and a second inflation lumen associated with the second cuff.

9. The tracheal tube of claim 6, wherein the second cuff comprise an S-shape.

10. The tracheal tube of claim 1, wherein the first distal end is located on the tracheal tube between a first cuff and a second cuff.

11. The tracheal tube of claim 1, wherein the tracheal tube is configured to be coupled to at least one of a ventilator, a bag for ventilation, inspiration valving, expiration valving, or an air supply.

12. The tracheal tube of claim 1, comprising a suction lumen terminating in a port located proximal to a first cuff.

13. The tracheal tube of claim 1, comprising a fluid delivery lumen associated with the camera, wherein the fluid delivery lumen is configured to supply fluid to a surface of the camera and remove buildup on the camera.

14. The tracheal tube of claim 1, wherein the camera is located on an interior surface of the second ventilation lumen.

15. The tracheal tube of claim 1, wherein the opening comprises a fenestration on a side wall of the second lumen.

16. The tracheal tube of claim 1, wherein the camera is disposed on a wall that at least in part comprises a dividing wall between the first ventilation lumen and the second ventilation lumen along its length.

17. The tracheal tube of claim 1, wherein an orientation of the camera is orthogonal to an airflow direction through the second ventilation lumen.

* * * * *